(12) United States Patent
Dholakia et al.

(10) Patent No.: US 10,942,023 B2
(45) Date of Patent: Mar. 9, 2021

(54) SPATIALLY OFFSET OPTICAL COHERENCE TOMOGRAPHY

(71) Applicant: UNIVERSITY COURT OF THE UNIVERSITY OF ST ANDREWS, Fife (GB)

(72) Inventors: Kishan Dholakia, Fife (GB); Mingzhou Chen, Fife (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 0 days.

(21) Appl. No.: 16/044,005

(22) Filed: Jul. 24, 2018

(65) Prior Publication Data
US 2019/0346252 A1    Nov. 14, 2019

(30) Foreign Application Priority Data
May 14, 2018    (GB) .................................... 1807783.4

(51) Int. Cl.
*G01B 9/02*    (2006.01)
(52) U.S. Cl.
CPC ....... *G01B 9/02091* (2013.01); *G01B 9/0203* (2013.01); *G01B 9/02041* (2013.01); *G01B 9/02082* (2013.01)
(58) Field of Classification Search
CPC .............. G01B 9/02091; G01B 9/0203; G01B 9/02082; G01B 9/02041
See application file for complete search history.

(56) References Cited

U.S. PATENT DOCUMENTS

| | | | | |
|---|---|---|---|---|
| 6,256,102 B1* | 7/2001 | Dogariu | ............. | G01B 9/02019 356/450 |
| 6,738,144 B1* | 5/2004 | Dogariu | ............. | G01N 15/0211 356/335 |
| 6,958,816 B1* | 10/2005 | Dogariu | ................. | G01N 11/02 356/479 |
| 7,925,133 B2* | 4/2011 | Bouma | .............. | G02B 6/02042 385/126 |
| 8,922,781 B2* | 12/2014 | Tearney | ............... | A61B 5/0066 356/479 |
| 9,618,325 B2* | 4/2017 | Brown | ............... | G01B 9/02091 |
| 9,968,261 B2* | 5/2018 | Motafakker-Fard | | ......................... A61B 5/0066 |

(Continued)

OTHER PUBLICATIONS

Zahid Yaqoob, Jigang Wu, and Changhuei Yang, "Spectral domain optical coherence tomography: a better OCT imaging strategy", BioTechniques 39:S6-S13 (Dec. 2005), doi 10.2144/000112090 (Year: 2005).*

(Continued)

*Primary Examiner* — Hwa Andrew Lee
(74) *Attorney, Agent, or Firm* — Moore & Van Allen PLLC; W. Kevin Ransom

(57) ABSTRACT

An optical coherence tomography system for imaging a sample is configured so as to illuminate a region of interest of the sample with incident light from an optical source. The optical coherence tomography system is further configured so as to interfere, on an optical detector, reference light from the optical source with offset returning light emerging from the sample along an offset collection path which is spatially offset from the region of interest of the sample, thereby creating interference on the optical detector.

21 Claims, 11 Drawing Sheets

(56) References Cited

U.S. PATENT DOCUMENTS

2015/0168125 A1* 6/2015 Arieli .................... A61B 3/102
   351/211
2015/0285685 A1* 10/2015 Wax ...................... G01J 3/2823
   356/456

OTHER PUBLICATIONS

International Search Report under Section 17 for GB1807783.4 dated Nov. 6, 2018.
Orly Liba, Matthew Lew, Elliott D. SoRelle, Rebecca Dutta, Debasish Sen, Darius M. Moshfeghi, Steven Chu, & Adam de la Zerda; Article: Speckle-modulating optical coherence tomography in living mice and humans; Nature Communications; Received Nov. 1, 2017; Accepted May 8, 2017; Published Jun. 20, 2017.
Thomas E. Matthews, Manuel Medina, Jason R. Maher, Howard Levinson, William J. Brown, and Adam Wax; Deep tissue imaging using spectroscopic analysis of multiply scattered light; Optica Research Article; vol. 1, No. 2, Aug. 2014; Optica 105; Received Apr. 23, 2014; Revised Jun. 25, 2014; Accepted Jun. 26, 2014; Published Aug. 13, 2014.
Larry K. Wong, Michael J. Mandella, Gordon S. Kino, and Thomas D. Wang; NIH Public Access—Author Manuscript; Improved rejection of multiply scattered photons in confocal microscopy using dual-axes architecture; Published in final edited form as Opt Lett; Jun. 15, 2007, 32(12); 1674-1676.
Yang Zhao, Will J. Eldridge, Jason R. Maher, Sanghoon Kim, Michael Cross, Mohamed Ibrahim, Howard Levinson, and Adam Wax; HHS Public Access—Dual-axis optical coherence tiomography for deep tissue imaging; Published in final edited form Jun. 15, 2017.
Thomas E. Mathews, Michael G. Giacomelli, William J. Brown, and Adam Wax; Fourier domain multispectral multiple scattering low coherence interferometry; Applied Optics; vol. 52, No. 34, Dec. 1, 2013.
Johanthan T. C. Liu, Michael J. Mandella, James M. Crawford, Christopher H. Contag, Thomas D. Wang, Gordon S. Kino; Efficient rejection of scattered light enables deep optical sectioning in turbid media with low-numerical-aperture optics in a dula-axis confocal architecture; Journal of Biomedical Optics—May/Jun. 2008, vol. 13 (3).

* cited by examiner

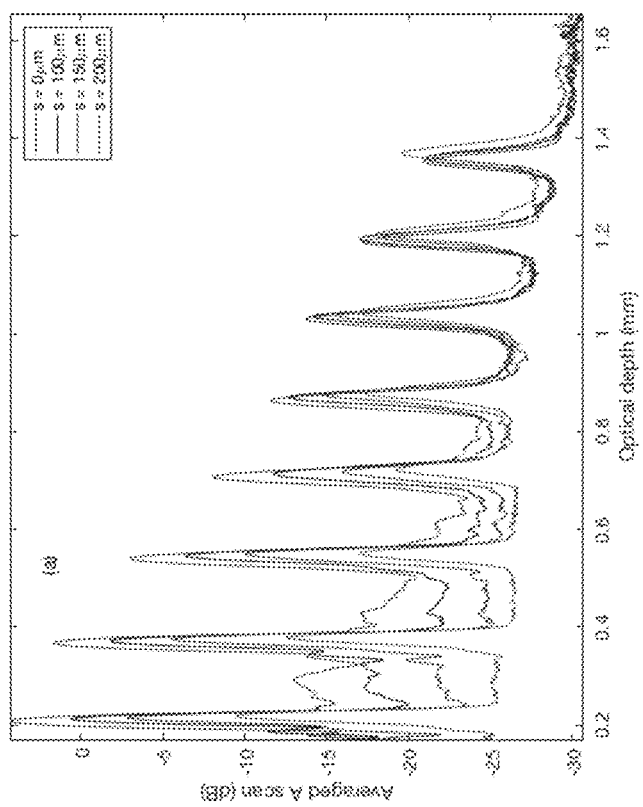
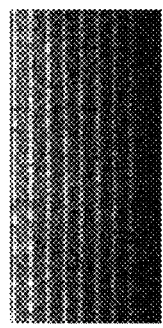
Fig. 3B
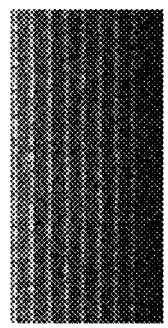
Fig. 3C
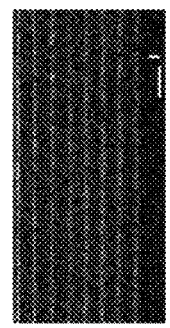
Fig. 3D
Fig. 3A

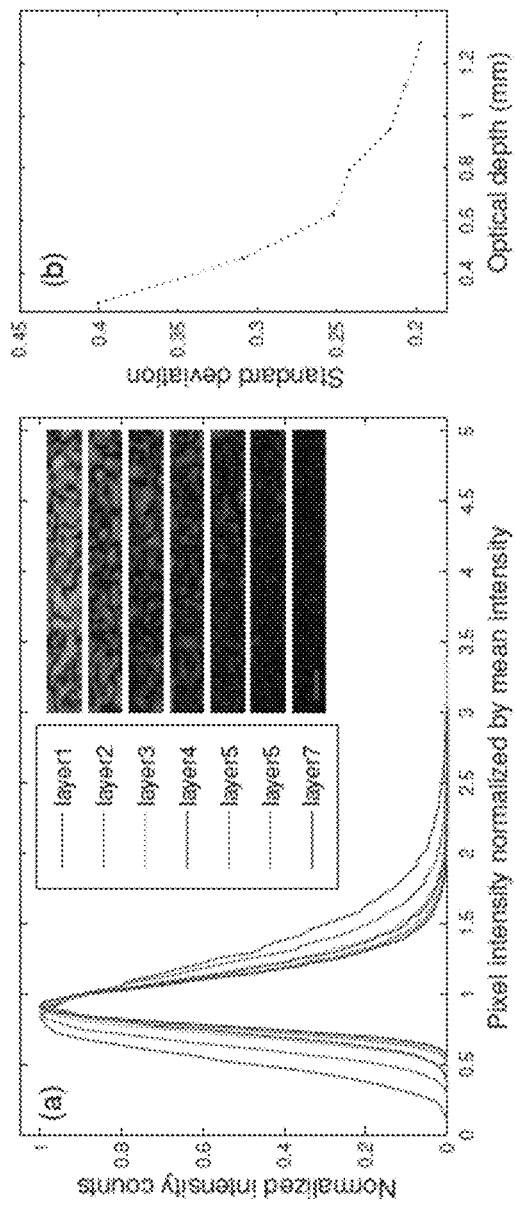
Fig. 4A
Fig. 4B
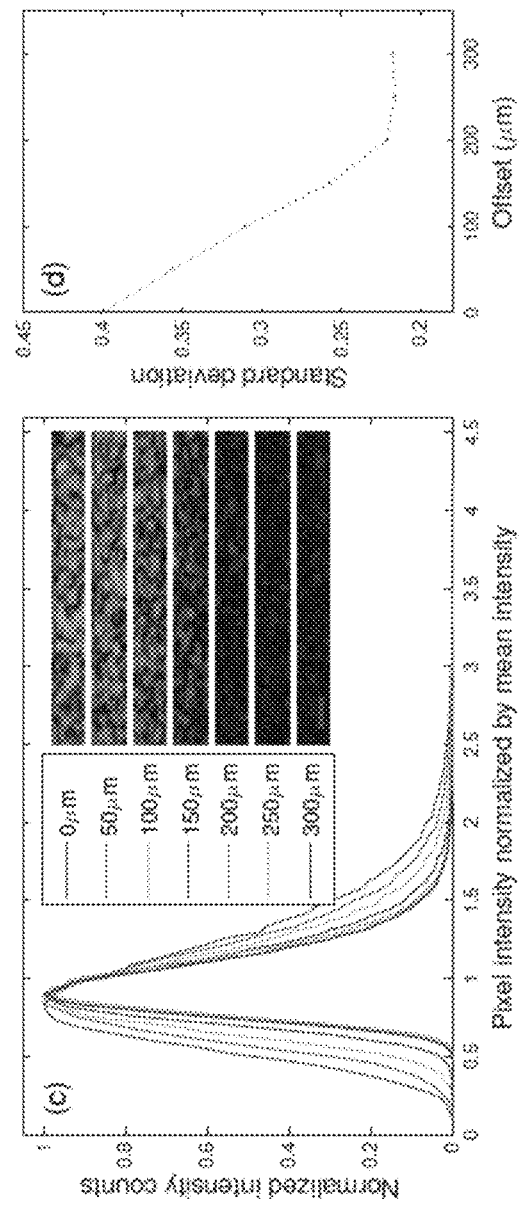
Fig. 4C
Fig. 4D

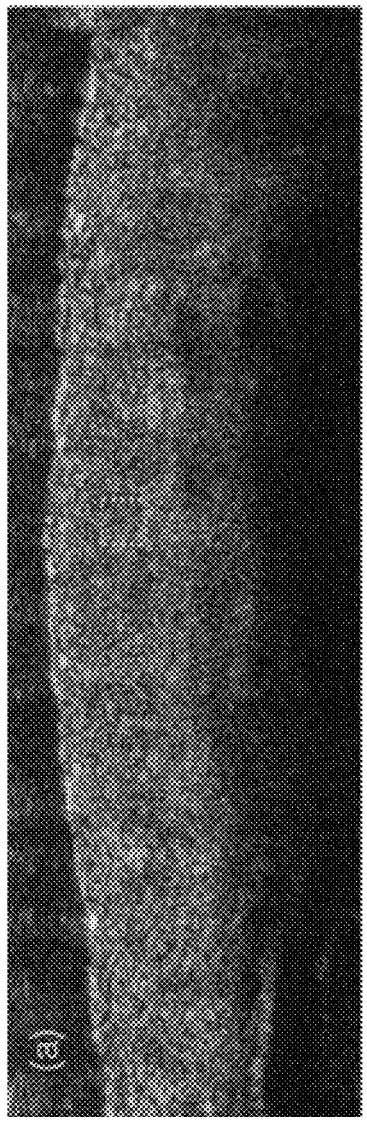
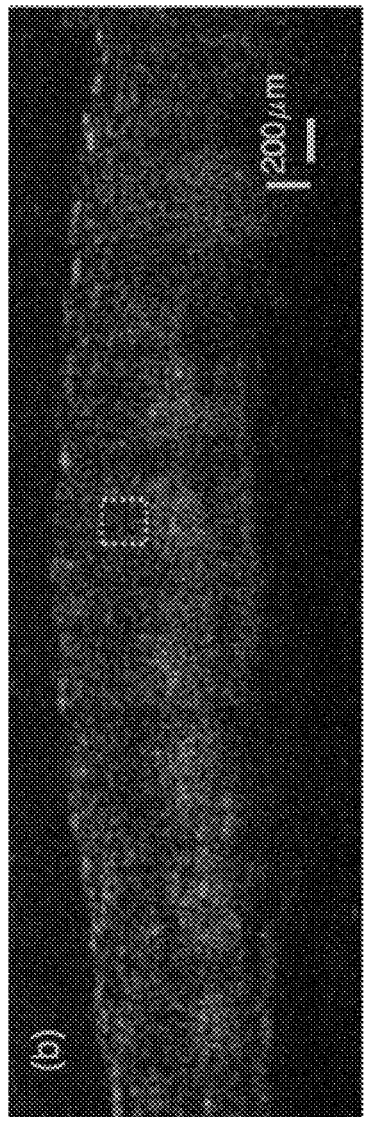
Fig. 7A
Fig. 7B

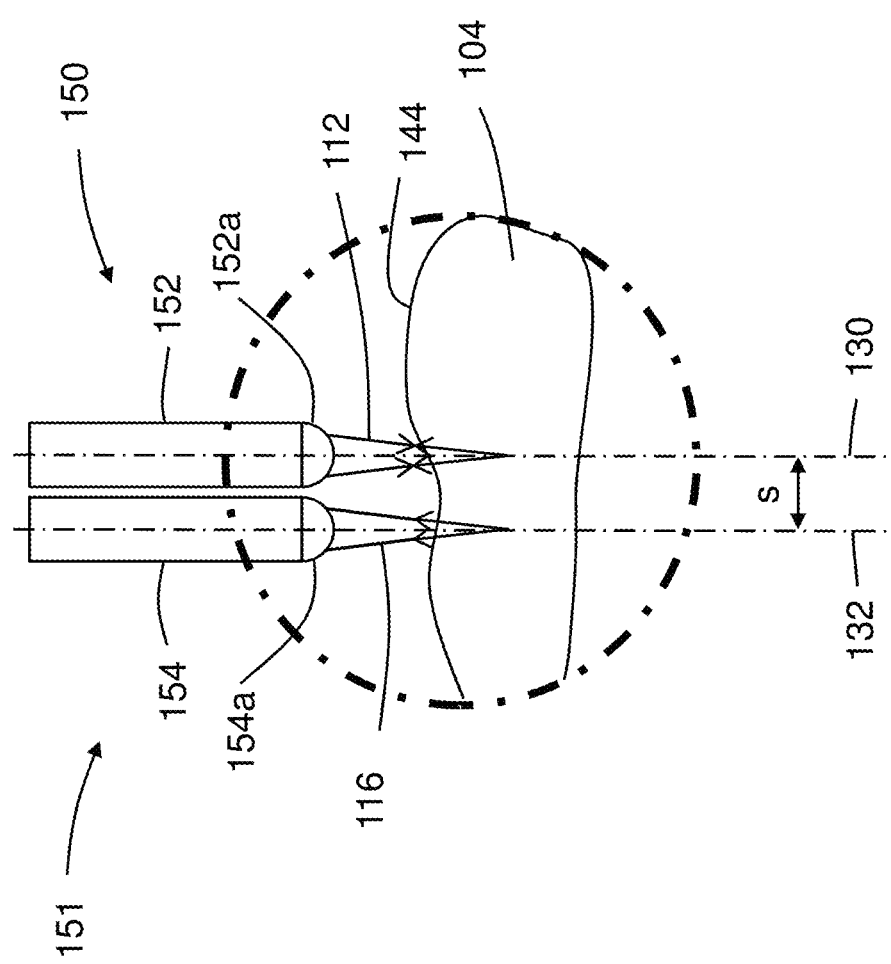

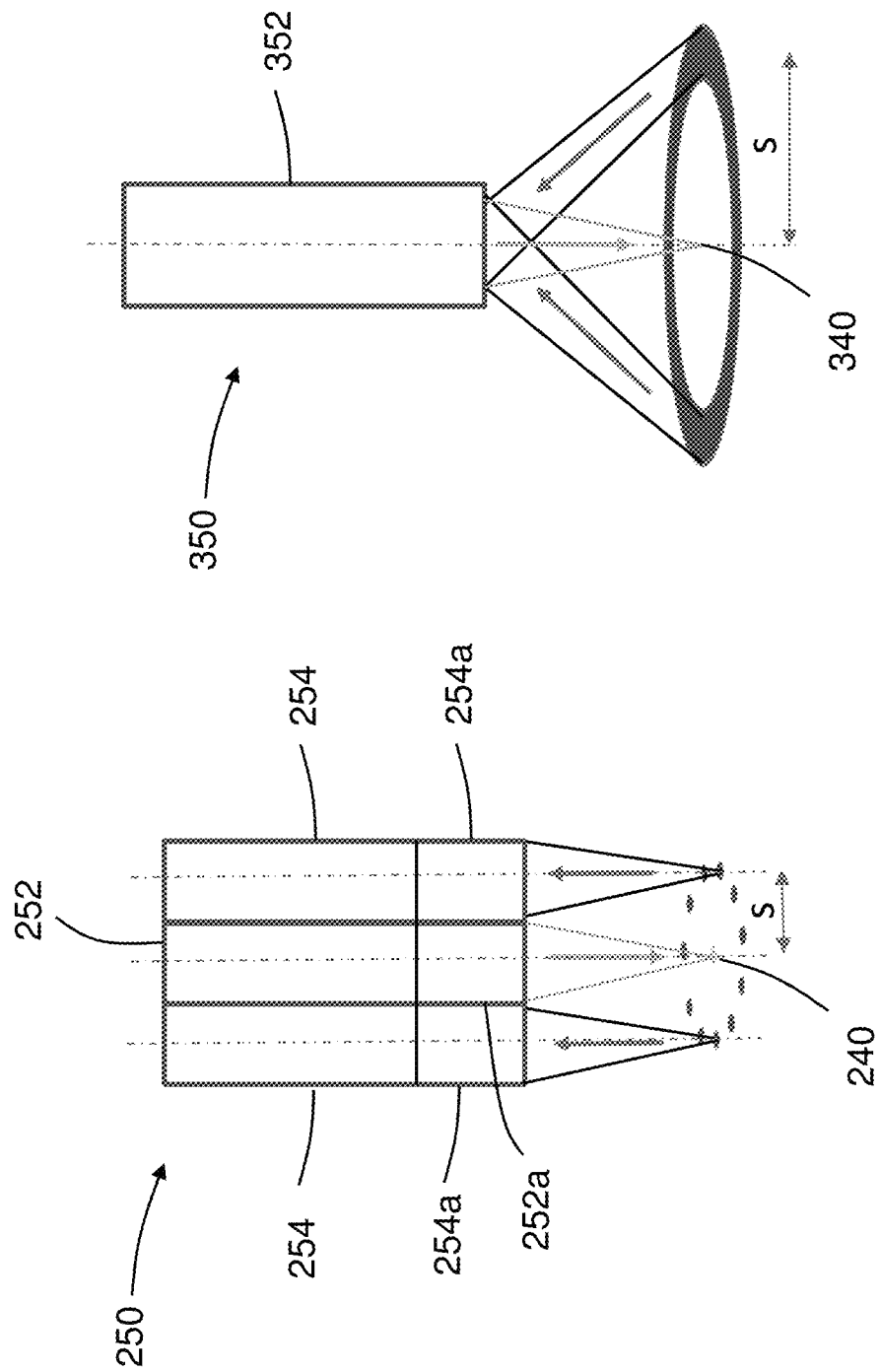

SPATIALLY OFFSET OPTICAL COHERENCE TOMOGRAPHY

CROSS-REFERENCE TO RELATED APPLICATION(S)

This application claims priority under 35 U.S.C. 119(a) to United Kingdom Application No. 1807783.4 filed May 14, 2018, the contents of which are also incorporated herein by reference.

FIELD OF THE INVENTION

The present disclosure relates to optical coherence tomography (OCT) systems and methods for imaging a sample and, in particular but not exclusively, a sample including a turbid medium such as biological sample or specimen.

BACKGROUND OF THE INVENTION

Known OCT systems may provide morphological information about a sample such as a biological sample or specimen. However, most biological samples or specimens are turbid with the result that speckle may dominate in an OCT image of a biological sample or specimen obtained obscuring or obfuscating any fine features of the biological sample or specimen especially at greater depths within the biological sample or specimen. As such, the penetration depth is often one of the key limitations of known OCT systems.

Newer techniques have been developed to reduce speckle in order to detect features which could not be previously detected or revealed in the speckle. However, most of these newer techniques use complex optical components which are difficult to align and/or which are expensive, such as spatial light modulators (SLMs), micro electromechanical systems (MEMS) mirrors or digital micromirrors.

SUMMARY OF THE INVENTION

It should be understood that any one or more of the features of any one of the following aspects of the present disclosure may be combined with any one or more of the features of any of the other aspects of the present disclosure.

According to an aspect of the present disclosure there is provided an optical coherence tomography system for imaging a sample, the system being configured so as to:

illuminate a region of interest of the sample with incident light from an optical source; and interfere, on an optical detector, reference light from the optical source with offset returning light emerging from the sample along an offset collection path which is spatially offset from the region of interest of the sample, thereby creating interference on the optical detector.

Such an OCT system may be used to obtain OCT images of finer features at greater depths within a turbid medium such as biological sample or specimen using simpler optical components than known OCT systems.

The sample may be turbid.

The sample may comprise a turbid medium.

The sample may comprise a biological sample or specimen such as tissue.

The region of interest may be located at least partially within the sample and/or on a surface of the sample.

The region of interest may comprise an object located at least partially within the sample and/or on a surface of the sample.

The object may be embedded in the sample.

The object may be turbid.

The object may comprise a structure.

The system may be configured so that the incident light converges as it is incident on the sample.

The system may be configured so that the offset returning light diverges as it emerges from the sample along the offset collection path so as to define a virtual image point in the sample on the offset collection path, the virtual image point being spatially offset from the region of interest.

The system may be configured so that the incident light propagates along an illumination path. The offset collection path may be parallel to, but spatially offset from, the illumination path.

The system may comprise the optical source and/or the optical detector.

The illumination path and the offset collection path may be straight line paths.

The system may comprise an optical splitter having an input optically coupled to the optical source and an optical combiner having an output optically coupled to the optical detector. The optical splitter and the optical combiner may define therebetween a measurement arm and a separate reference arm, wherein the sample is located in the measurement arm and the reference arm defines a reference path for the reference light. The optical combiner may be configured to combine the offset returning light with the reference light to form combined light at the output of the optical combiner.

In such a system, the measurement arm and the reference arm are effectively decoupled. Specifically, the illumination path, the offset collection path and the reference path are all decoupled.

The optical splitter may comprise a bulk optical beam splitter or an optical fibre splitter. Similarly, the optical combiner may comprise a bulk optical beam combiner or an optical fibre combiner.

The optical splitter and the optical combiner may define a Mach-Zehnder interferometer.

The system may comprise an optical coupling arrangement in the measurement arm, the optical coupling arrangement being configured to illuminate the region of interest of the sample with the incident light from the optical source and to collect the offset returning light emerging from the sample.

The optical coupling arrangement may comprise a lens such as an objective lens.

The system may comprise an offset lens in the measurement arm between the optical coupling arrangement and the optical combiner, wherein the offset lens is configured to optically couple the offset returning light to the optical combiner so as to combine the offset returning light with the reference light to form the combined light.

The offset lens may define an offset lens optical axis. The combined light may propagate along a combined light optical axis. The offset lens optical axis may be parallel to, but spatially offset from, the combined light optical axis.

The offset lens may be movable so as to vary the spatial offset between the offset lens optical axis and the combined light optical axis and thereby vary the spatial offset between the offset collection path and the region of interest.

The offset lens may be movable so as to reduce the spatial offset between the offset lens optical axis and the combined light optical axis to zero and thereby reduce the spatial offset between the offset collection path and the region of interest to zero. Such a system may be used to obtain an OCT image for any spatial offset between the offset collection path and the region of interest including a spatial offset of zero. This may allow the comparison of OCT images obtained for different spatial offsets. This may allow the selection of an optimum spatial offset for optimum OCT image quality. For example, this may allow the selection of an optimum spatial offset which minimizes the signal-to-noise ratio (SNR) of an OCT image of the region of interest of the sample.

The optical coupling arrangement may comprise a multi-mode optical waveguide such as a multi-mode optical fibre.

The system may comprise an input optical coupling arrangement in the measurement arm, the input optical coupling arrangement being configured to illuminate the region of interest of the sample with the incident light from the optical source. The system may comprise an output optical coupling arrangement in the measurement arm, the output optical coupling arrangement being spatially offset from the input optical coupling arrangement so as to collect the offset returning light.

The input optical coupling arrangement may comprise an input optical waveguide such as an input optical fibre. The input optical coupling arrangement may comprise an input lens. The input lens may be formed on, or attached to, an output end of the input optical waveguide. The input lens may comprise a microlens or a GRIN lens.

The output optical coupling arrangement may comprise an output optical waveguide such as an output optical fibre. The output optical coupling arrangement may comprise an output lens. The output lens may be formed on, or attached to, an input end of the output optical waveguide. The output lens may comprise a microlens or a GRIN lens.

The input optical coupling arrangement may comprise a plurality of input optical waveguides such as a plurality of input optical fibres. The input optical coupling arrangement may comprise a plurality of input lenses. Each input lens may be formed on, or attached to, an output end of a corresponding input optical waveguide. Each input lens may comprise a microlens or a GRIN lens.

The output optical coupling arrangement may comprise a plurality of output optical waveguides such as a plurality of output optical fibres. The output optical coupling arrangement may comprise a plurality of output lenses. Each output lens may be formed on, or attached to, an input end of a corresponding output optical waveguide. Each output lens may comprise a microlens or a GRIN lens.

The optical source may comprise a broadband light source. The optical source may comprise a superluminescent laser diode or a light emitting diode.

The system may comprise a dispersive element for spatially dispersing the interference across the image sensor according to a wavelength of the interference.

The dispersive element may comprise a diffraction grating.

The optical detector comprises an image sensor.

The image sensor may be configured to detect the spatial distribution of the spatially dispersed interference.

The system may comprise a controller.

The controller may be configured for communication with the optical detector.

The controller may be configured to use an inverse Fourier transform to convert the spatial distribution of the spatially dispersed interference into an optical coherence tomography image of the sample as a function of depth through the sample.

The system may comprise first and second image sensors, wherein the system is configured to couple zero-order diffracted light to the first image sensor and higher-order diffracted light, for example first-order diffracted light, to the second image sensor. The use of such first and second image sensors may allow the spatial offset between the illumination path and the offset collection path to be calibrated in advance of any OCT measurements according to the configuration, nature and/or properties of the sample.

The optical source may comprise a narrowband light source or a coherent light source.

The optical source may comprise a laser or an optical parametric oscillator (OPO).

The optical source may be tunable.

The controller may be configured for communication with the optical source.

The controller may be configured to:
vary a wavelength of the optical source;
use the optical detector to detect the interference as a function of wavelength of the optical source to provide an optical spectrum of the interference; and
use an inverse Fourier transform to convert the optical spectrum of the interference into an optical coherence tomography image of the sample as a function of depth through the sample.

The system may comprise a variable optical element configured to vary an optical length of a reference path for the reference light. For example, the variable optical element may comprise a movable mirror.

The controller may be configured for communication with the variable optical element.

The controller may be configured to:
control the variable optical element so as to vary the optical length of the reference path across a range of optical lengths selected to match a range of depths in the sample; and
use the optical detector to detect the interference as a function of the optical length of the reference path to provide an optical coherence tomography image of the sample as a function of depth through the sample.

The offset lens may be mounted on a motorized translation stage.

The controller may be configured for communication with the motorized translation stage.

The controller may be configured to control the motorized translation stage so as to vary the spatial offset between the illumination path and the offset collection path to optimize a signal-to-noise ratio (SNR) associated with the optical coherence tomography image of the sample.

According to an aspect of the present disclosure there is provided an optical coherence tomography method for imaging a sample, the method comprising:
illuminating a region of interest of the sample with incident light from an optical source; and
interfering, on an optical detector, reference light from the optical source with offset returning light emerging from the sample along an offset collection path which is spatially offset from the region of interest of the sample, thereby creating interference on the optical detector.

The incident light may converge as it is incident on the sample.

The offset returning light may diverge as it emerges from the sample along the offset collection path so as to define a virtual image point in the sample on the offset collection path, the virtual image point being spatially offset from the region of interest.

The incident light may propagate along an illumination path.

The offset collection path may be parallel to, but spatially offset from, the illumination path.

The method may comprise using a multi-mode optical waveguide, such as a multi-mode optical fibre, to illuminate the region of interest of the sample with the incident light from the optical source and so as to collect the offset returning light emerging from the sample.

The method may comprise transmitting light from an input side of the multi-mode optical waveguide through the multi-mode optical waveguide and focussing the transmitted light onto the region of interest of the sample whilst also collecting offset returning light emerging from an annular region of the sample located around the region of interest and transmitting the returning light back through the multi-mode optical waveguide to an input side of the multi-mode optical waveguide.

The method may comprise characterizing the multi-mode optical waveguide in terms of phase and, optionally, also in terms of amplitude and/or polarization to generate characterization results for the multi-mode optical waveguide.

The method may comprise characterizing the multi-mode optical waveguide in terms of phase and, optionally, also in terms of amplitude and/or polarization by measuring the amplitude and phase distribution of one or more polarization components of an output optical field on an output side of the multi-mode optical waveguide for a plurality of input optical fields on an input side of the multi-mode optical waveguide, wherein each input optical field is orthogonal to the other input optical fields. Each input optical field may, for example, be orthogonal to the other input optical fields in at least one of phase, amplitude and polarization.

The method may comprise using the characterization results for the multi-mode optical waveguide to select the phase and, optionally, also the amplitude and/or polarization of an input optical field at an input side of the multi-mode optical waveguide so as to illuminate the region of interest of the sample with a desired output optical field from the optical source and so as to collect the offset returning light emerging from the sample along the offset collection path at the output side of the multi-mode optical waveguide.

The method may comprise using the characterization results for the multi-mode optical waveguide to select the phase and, optionally, also the amplitude and/or polarization of an input optical field at an input side of the multi-mode optical waveguide so as to focus the incident light from the optical source onto the region of interest of the sample whilst also collecting offset returning light emerging from an annular region of the sample located around the region of interest and transmitting the returning light back through the multi-mode optical waveguide to the input side of the multi-mode optical waveguide.

The method may comprise using the characterization results for the multi-mode optical waveguide to select the phase and, optionally, also the amplitude and/or polarization of an input optical field at an input side of the multi-mode optical waveguide so as to illuminate an annular region of interest of the sample with the incident light from the optical source whilst also collecting offset returning light emerging from a central region of the sample located within the annular region of interest and transmitting the returning light back through the multi-mode optical waveguide to the input side of the multi-mode optical waveguide.

The optical source may comprise a broadband light source. The optical source may comprise a superluminescent laser diode or a light emitting diode.

The optical detector may comprise an image sensor.

The method may comprise:

spatially dispersing the interference across the image sensor according to a wavelength of the interference;

using the image sensor to detect a spatial distribution of the spatially dispersed interference; and using an inverse Fourier transform to convert the spatial distribution of the spatially dispersed interference into an optical coherence tomography image of the sample as a function of depth through the sample.

The optical source may comprise a narrowband light source or a coherent light source.

The optical source may comprise a laser or an optical parametric oscillator (OPO).

The optical source may be tunable.

The method may comprise:

varying a wavelength of the optical source;

detecting the interference as a function of the wavelength of the optical source to provide an optical spectrum of the interference; and using an inverse Fourier transform to convert the optical spectrum of the interference into an optical coherence tomography image of the sample as a function of depth through the sample.

The method may comprise:

varying an optical length of a reference path for the reference light across a range of optical lengths selected to match a range of depths in the sample; and detecting the interference as a function of the optical length of the reference path to provide an optical coherence tomography image of the sample as a function of depth through the sample.

The method may comprise varying the spatial offset between the offset collection path and the region of interest to optimize a signal-to-noise ratio (SNR) associated with the optical coherence tomography image of the region of interest.

BRIEF DESCRIPTION OF THE DRAWINGS

OCT systems and methods will now be described by way of non-limiting example only with reference to the following drawings of which:

FIG. 3A is an averaged A scan of a 7-layer-nescofilm phantom with different offset collection path offsets;

FIG. 3B shows a B scan at an offset collection path offset of 0 μm;

FIG. 3C shows a B scan at an offset collection path offset of 100 μm;

FIG. 3D shows a B scan at an offset collection path offset of 200 μm;

FIG. 4A shows the histograms of normalized speckle fields in different layers of a 7-layer nescofilm for an offset collection path offset of 0 μm;

FIG. 4B shows the standard deviations of the normalized speckle fields of FIG. 4A in different layers as a function of depth for an offset collection path offset of 0 μm;

FIG. 4C shows the histograms of normalized speckle fields in the first layer of a 7-layer nescofilm for different offset collection path offsets;

FIG. 4D shows the standard deviations of the normalized speckle fields of FIG. 4C in the first layer of the 7-layer nescofilm as a function of offset collection path offset;

FIG. 7A shows a B scan performed on a region of a Zebra fish for an offset collection path offset of 0 μm;

FIG. 7B shows a B scan performed on the same region of the same Zebra fish as the B scan of FIG. 7A for an offset collection path offset of 50 μm;

FIG. 8B is a detailed schematic of the optical coupling arrangements of the alternative OCT system of FIG. 8A used to couple light to and from the sample;

FIG. 8C shows an alternative optical coupling arrangement for an OCT system for coupling light to and from a sample; and FIG. 8D shows a further alternative optical coupling arrangement for an OCT system for coupling light to and from a sample.

DETAILED DESCRIPTION OF THE INVENTION

Figure 1A:
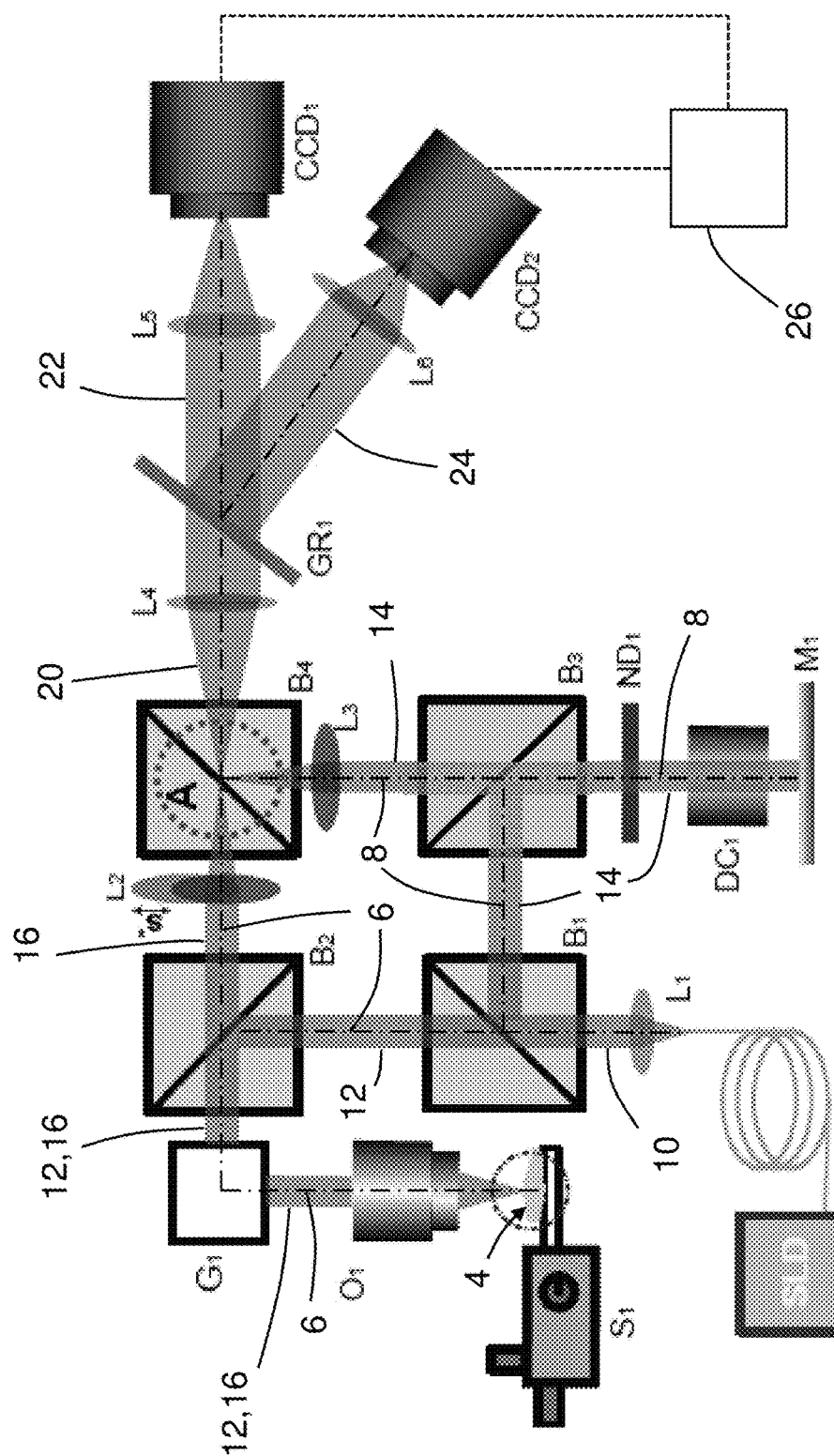
FIG. 1A is a schematic illustration of an OCT system for imaging a sample.

Referring initially to FIG. 1A there is shown an OCT system generally designated 2 for imaging a sample generally designated 4. The system 2 includes an optical source in the form of a superluminescent diode laser SLD (S850, Superlum, central wavelength 800 nm with bandwidth 14 nm) and first and second detectors in the form of first and second image sensors, CCD1 (CCD camera, FL3-U3-32S2M-CS, Point Grey) and CCD2 (GigE Vision line scan camera, Aviiva EM1,Teledyne).

The system 2 is configured to couple light from the optical source SLD to the sample 4 and to couple light collected from the sample 4 to the first and second image sensors, CCD1, CCD2. More specifically, the system 2 includes a 90/10 transmitting/reflecting non-polarizing beam splitter B1 and a 50/50 transmitting/reflecting non-polarizing beam combiner B4 which together define a Mach-Zehnder interferometer having a measurement arm generally designated 6 including the sample 4, and a separate reference arm generally designated 8. The system 2 further includes a single mode fibre SMF1 and a coupling lens L1 for coupling light from the optical source SLD to the beam splitter B1.

In the measurement arm 6 between the beam splitter B1 and the sample 4, the system 2 includes a further 50/50 transmitting/reflecting non-polarizing beam splitter B2, a 2D galvo mirror G1, and an optical coupling arrangement in the form of a microscope objective O1 having an effective focal length of 36 mm. The system 2 includes a 3D sample translation stage S1 for translating the sample 4. The system 2 further includes a movable coupling lens L2 in the measurement arm 6 between the beam splitter B2 and the beam combiner B4. One of skill in the art will understand that the movable coupling lens L2 may be mounted in a lens mount (not shown) which is attached to a translation stage (not shown) for movement of the coupling lens L2.

In the reference arm 8 between the beam splitter B1 and the beam combiner B4, the system 2 includes a further 50/50 transmitting/reflecting non-polarizing beam splitter B3, a neutral density filter ND1, dispersion compensation DC1, and a fixed reference mirror M1. The system 2 further includes a coupling lens L3 in the reference arm 8 between the beam splitter B3 and the beam combiner B4.

The system 2 further includes a dispersive element in the form of a transmissive diffraction grating GR1 (1200 lines/mm, coated for 700 to 960 nm), a coupling lens L4 for coupling light from the beam combiner B4 to the diffraction grating GR1, a coupling lens L5 for coupling zero-order diffracted light from the diffraction grating GR1 to the first image sensor CCD1 and a coupling lens L6 for coupling first-order diffracted light from the diffraction grating GR1 to the second image sensor CCD2.

The system 2 further includes a controller 26 configured for communication with the first and second image sensors CCD1 and CCD2.

In use, the beam splitter B1 splits light 10 from the optical source SLD into incident light 12 propagating in the measurement arm 6 and reference light 14 propagating in the reference arm 8. The incident light 12 is coupled to the sample 4 via the beam splitter B2, the 2D galvo mirror G1 and the objective O1. After interaction with the sample 4, returning light 16 returns from the sample 4 and is collected by the objective O1 and coupled through the 2D galvo mirror G1, the beam splitter B2 and the movable coupling lens L2 to the beam combiner B4.

The reference light 14 is coupled to the reference mirror M1 via the beam splitter B3, the neutral density filter ND1 and the dispersion compensation DC1. The reference mirror M1 reflects the reference light 14 back through the dispersion compensation DC1, the neutral density filter ND1 and the beam splitter B3 and the coupling lens L3 to the beam combiner B4.

As will be described in more detail below, the beam combiner B4 combines the returning light 16 with the reference light 14 resulting in interference at the first image sensor CCD1 and interference at the second image sensor CCD2. Specifically, the beam combiner B4 combines the returning light 16 with the reference light 14 to form combined light 20 which is coupled by the coupling lens L4 to the diffraction grating GR1. Lens L5 couples zero-order diffracted light 22 from the diffraction grating GR1 to the first image sensor CCD1 resulting in interference at the first image sensor CCD1. Lens L6 couples first-order diffracted light 24 from the diffraction grating GR1 to the second image sensor CCD2 resulting in interference at the second image sensor CCD2.

The second image sensor CCD2 detects the spatial distribution of the first-order diffracted light 24 to thereby generate an electrical signal representative of the spatial distribution of the first-order diffracted light 24. As one of skill in the art will understand, as a consequence of the interference between the returning light 16 and the reference light 14 at the second image sensor CCD2, the spatial distribution of the first-order diffracted light 24 is representative of an optical spectrum of the collected returning light 16. Moreover, the controller 26 is configured to use an inverse Fourier transform to convert the first-order diffracted light 24 into an OCT image of the sample 4 as a function of depth through the sample 4.

As described with reference to FIGS. 1B and 1C, the objective $O_1$ illuminates the sample 4 using the incident light 12 from the optical source SLD such that the incident light 12 is incident on the sample 4 along an illumination path 30 which forms part of the measurement arm 6. Moreover, as will be described in more detail below, the system 2 is capable of interfering, at the first and second image sensors CCD1, CCD2, the reference light 14 from the optical source SLD with a portion of the returning light 16, referred to herein as "offset returning light", which is collected from the sample 4 along an offset collection path 32 which is spatially offset from a region of interest of the sample 4. In the specific example of the system 2 described with reference to FIGS. 1A and 1B, the offset collection path 32 is parallel to, but spatially offset from, the illumination path 30 by a distance s which is determined according to the position of the movable coupling lens L2.

Figure 1B:
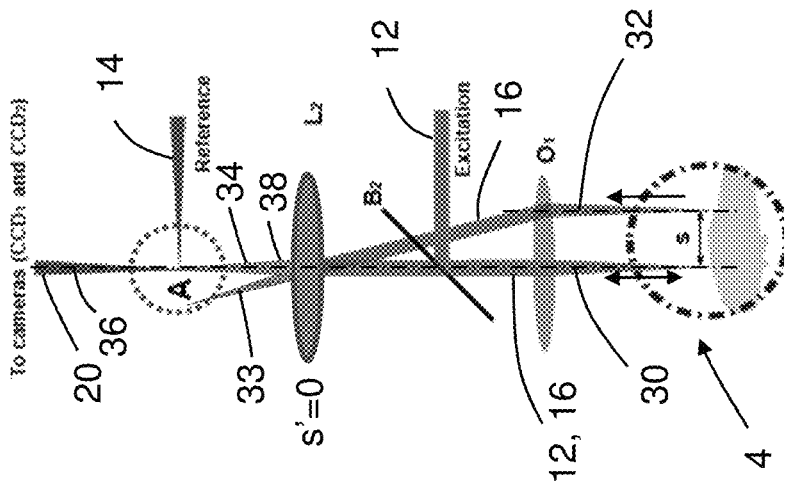
FIG. 1B illustrates the operation of the OCT system of FIG. 1A when light from an optical source is focussed so as to form incident light which converges on a region of interest of the sample and reference light is interfered with offset returning light emerging from the sample along an offset collection path which is spatially offset from the region of interest.
Figure 1C:
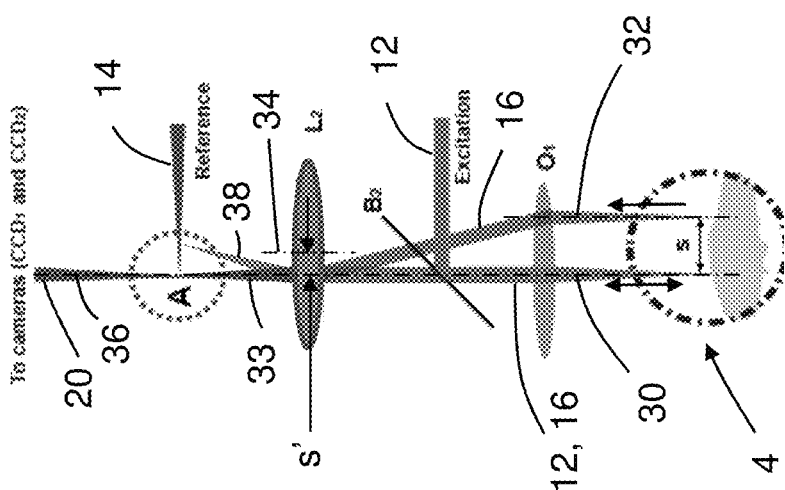
FIG. 1C illustrates the operation of the OCT system of FIG. 1A when light from an optical source is focussed so as to form incident light which converges on a region of interest of the sample along an illumination path and reference light is interfered with returning light emerging from the sample back along the illumination path.

FIG. 1B illustrates the collection of returning light 16 from the sample 4 and the combination of a portion 33 of the returning light 16, referred to herein as the offset returning light 33 with the reference light 14 to form the combined light 20 for the case when an optical axis 34 of the movable coupling lens L2 is offset laterally by a distance s' from an optical axis 36 of the combined light 20. As a consequence of the lateral offset s', a portion 38 of the returning light 16 which emerges from the sample 4 back along the illumination path 30 is refracted by the movable coupling lens L2 in a direction at an angle to the optical axis 36 of the combined light 20 without interfering with the reference light 14, whereas a portion 33 of the returning light 16 which emerges from the sample 4 along the offset collection path 32 is refracted by the movable coupling lens L2 along the optical axis 36 of the combined light 20 and interferes with the reference light 14.

Moreover, the movable coupling lens L2 may be movable laterally so as to reduce the lateral offset s' to zero as shown in FIG. 10, whereupon the portion 38 of the returning light 16 which emerges from the sample 4 back along the illumination path 30 propagates along the optical axis 36 of the combined light 20 interferes with the reference light 14, whereas the offset returning light 33 propagates at an angle to the optical axis 36 of the combined light 20 without interfering with the reference light 14.

From the foregoing description, one of ordinary skill in the art will understand that the lateral offset s' between the optical axis 34 of the movable coupling lens L2 and the optical axis 36 of the combined light 20 may be selected so as to interfere the offset returning light 33 emerging from the sample along an offset collection path which is parallel to, but spatially offset from, the illumination path 30 by a distance s. Moreover, the relationship between s' and s may be determined in advance of the OCT measurements by performing a calibration procedure in which a position of the zero-order diffracted light 22 on CCD1 is measured as a function of s'. In this way, it is very easy to acquire OCT images with or without a spatial offset s between the offset collection path 32 and the illumination path 30 in order to compare OCT measurement performance.

Figure 2:
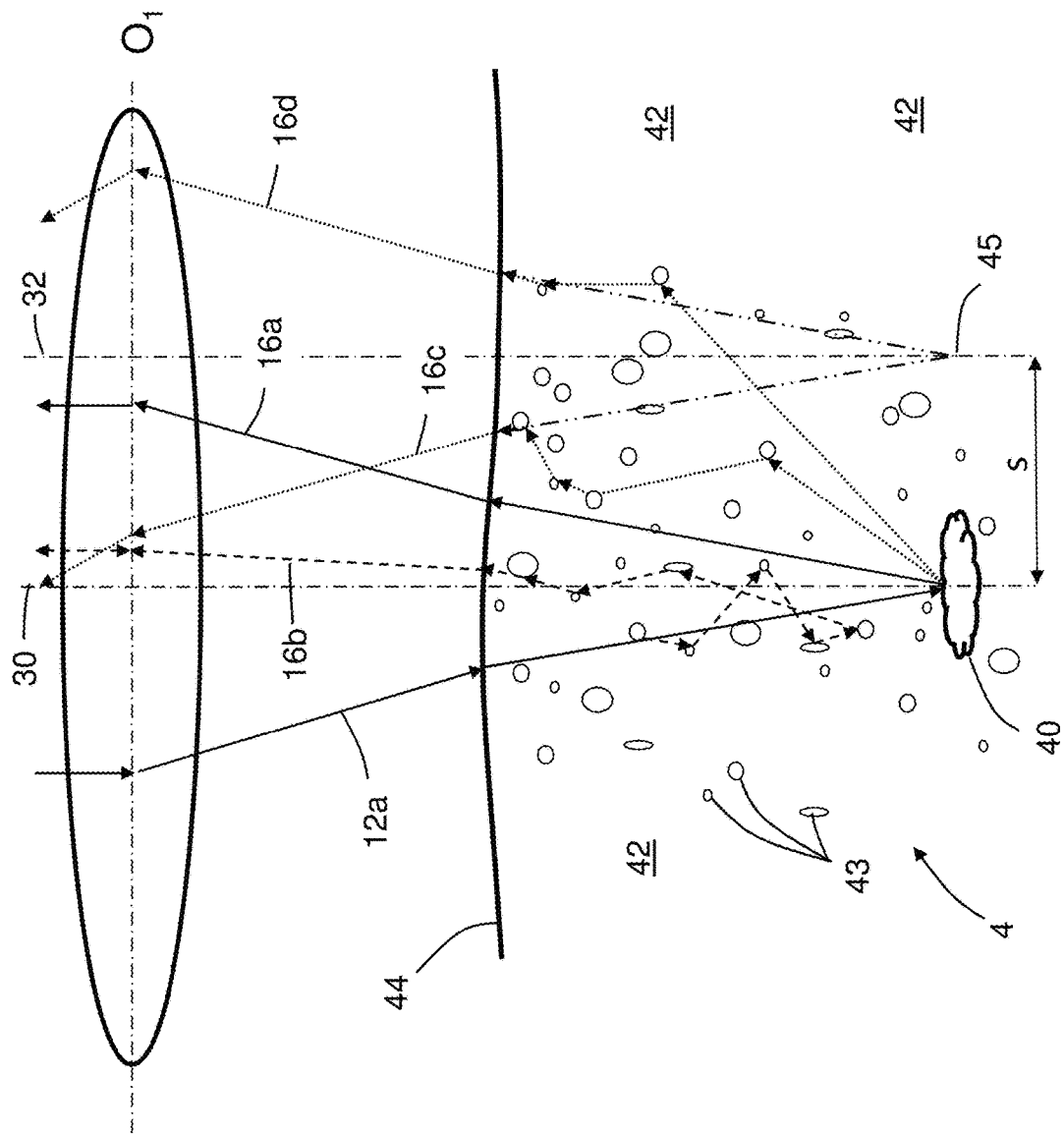
FIG. 2 illustrates the scattering of light within the sample of FIG. 1A.

FIG. 2 illustrates the principle of the offset OCT method described above with reference to the microscopic structure of the sample 4. As shown in FIG. 2, the sample 4 includes a scattering or turbid material 42 having multiple scatterers 43. The sample 4 further includes a region of interest 40 which may be a structure within the sample 4 or an object embedded within the sample 4. One of skill in the art will understand that FIG. 2 shows a single ray of light 12a incident upon a surface 44 of the sample 4 and a selection of rays of light 16a, 16b, 16c, and 16d emerging from the surface 44 of the sample 4 for the purposes of illustration only and that, in reality, a solid angle of light 12 is incident upon the sample 4 along the illumination path 30 and returning light 16 emerges from the surface 44 of the sample 4 across a range of different positions and with a range of different angles. One of ordinary skill in the art will also understand that the proportions of the objective lens O1 and the sample 4 shown in FIG. 2 have been selected for the purposes of illustration only and that, in reality, the proportions of the objective lens O1 and the sample 4 may be different to those shown in FIG. 2.

Intuitively, illuminating the sample 4 along the illumination path 30 and interfering offset returning light collected along the offset collection path 32 with the reference light 14 means that the returning light which is interfered with the reference light 14 to create the OCT image excludes at least some of the returning light which is back-scattered from that portion of the turbid material 42 which lies between the sample surface 44 and the region of interest 40. As will be described in more detail below, this may improve the signal-to-noise ratio (SNR) of the OCT image.

Incident light 12 entering the sample 4 may undergo a number of scattering events at one or more of the scatterers 43 and/or at the region of interest 40. For example, some of the photons of the incident ray 12a may pass directly through the scattering material 42, may be scattered from the region of interest 40, and may pass directly through the scattering material 42 to form a returning ray 16a. Such photons may be termed ballistic or singly scattered photons. The objective O1 collects and collimates returning ray 16a in a direction which is parallel to the illumination path 30.

However, some of the photons of the incident ray 12a may undergo many scattering events and may emerge from the surface 44 of the sample 4 without ever reaching the region of interest 40 to form a returning ray 16b. Such photons may be termed multiply-scattered photons. The position and the angle of returning ray 16b with respect to the surface 44 of the sample 4 is such that the objective O1 collects and collimates returning ray 16b in a direction which is parallel to the illumination path 30. If the optical path lengths associated with returning rays 16a and 16b within the sample 4 differ by less than a coherence length of the optical source SLD and the movable coupling lens L2 has a lateral offset s'=0 so as to interfere returning rays 16a and 16b with the reference light 14 in the OCT image of the region of interest 40 at the image sensor CCD2, returning ray 16b may contribute to speckle in the OCT image of the region of interest 40, thereby reducing the signal-to-noise ratio of the OCT image of the region of interest 40 potentially leading to obfuscation of the OCT image of the region of interest 40. If the optical path lengths associated with returning rays 16a and 16b within the sample 4 differ by much more than the coherence length of the optical source SLD and the movable coupling lens L2 has a lateral offset s'=0, then returning ray 16b may contribute to speckle in the OCT image at a depth other than the depth of the region of interest 40.

Some of the photons of the incident ray 12a may undergo a relatively limited number of scattering events before and/or after being scattered from the region of interest 40. Such photons may be termed quasi-ballistic photons. For example, the photons of returning rays 16c and 16d undergo a relatively limited number of further scattering events after being scattered by the region of interest 40 but before emerging from the sample surface 44. Specifically, returning ray 16c undergoes four scattering events after being scattered by the region of interest 40 but before emerging from the sample surface 44, whereas returning ray 16d undergoes two scattering events after being scattered by the region of interest 40 but before emerging from the sample surface 44. The respective positions and angles of returning rays 16c and 16d with respect to the surface 44 of the sample 4 are such that returning rays 16c and 16d appear to emerge from a position or virtual image point 45 within the sample 4, which position 45 is located on the offset collection path 32 and which position 45 is spatially offset from the region of interest 40. The objective O1 collects and collimates returning rays 16c and 16d parallel to one another in a direction at an angle to the offset collection path 32. Returning rays 16c and 16d have an optical path length difference within the sample 4 which is less than a coherence length associated with the optical source SLD. Consequently, if the lateral offset s' of the movable coupling lens L2 is selected so as to interfere returning rays 16c and 16d with the reference light 14 as described above with reference to FIG. 1B, returning rays 16c and 16d will both contribute to the offset returning light 33 and therefore the OCT image of the region of interest 40 at the image sensor CCD2.

Without wishing to be bound by theory, it is believed that the distribution of multiply scattered photons associated with returning rays such as returning ray 16b decays more rapidly with distance in a direction lateral to the illumination path 30 than the distribution of quasi-ballistic photons associated with returning rays such as returning rays 16c and 16d. Similarly, it is believed that the distribution of quasi-ballistic photons associated with returning rays such as returning rays 16c and 16d decays more rapidly with distance in a direction lateral to the illumination path 30 than the distribution of ballistic photons associated with returning rays such as returning ray 16a. Consequently, although the total amount of light returning along the offset collection path 32 is less than the total amount of light returning along the illumination path 30, the light returning along the offset collection path 32 includes a greater proportion of quasi-ballistic photons and a smaller proportion of multiply scattered photons. Consequently, interfering offset returning light 33 collected along the offset collection path 32 with the reference light 14 results in the interference of a greater proportion of quasi-ballistic photons with the reference light 14 and the interference of a smaller proportion of multiply scattered photons with the reference light 14, thereby improving the SNR of the OCT image of the region of interest 40 of the sample 4 obtained at the image sensor CCD2.

Experimental Results and Analysis on Phantoms

FIGS. 3A-3D show experimental results obtained using the OCT system 2 illustrating the change in speckle observed for different spatial offsets s for a scattering phantom formed of seven layers of nescofilm (120 µm for one single layer). Due to its strong scattering properties, layered nescofilm is an excellent phantom for modelling turbid media. B scans were acquired over a depth range of 1 mm by translating the sample 4 in one direction relative to the objective O1 using the sample translation stage S1. By adjusting the movable coupling lens L2, B scans were acquired over a depth range of 1 mm for different offsets s between the illumination path 30 and the offset collection path 32: s=0; 100; 150; 200 µm. The layers were purposely aligned perpendicular to the incident light 12 in order to obtain the averaged A scans, as shown in FIG. 3A. From these A scans, one can clearly identify positions and intensities at the peaks for the layer-layer interfaces. The peak intensity is attenuated due to the scattered photons from the layer-layer interface and diminishes for the deeper layers. The background intensity in layers, mainly speckle caused by the multiple scattered photons, is also attenuated for the deep layers. However, the background intensity is also reduced when the offset s is increased. FIGS. 3B-3D show the B scans for different offsets s. The scale bars shown in FIG. 3D indicate 100 µm. In the B scans of FIGS. 3B-3D, it can be clearly seen that the background intensity is reduced when the offset s is increased. Such a small offset does not, however, significantly reduce the signals from the layer-layer interfaces.

FIGS. 4A and 4B illustrate the results of a statistical analysis of attenuation of the speckle fields with depth within the seven layers of the nescofilm. The normalized histograms for each layer shown in FIG. 4A were generated by normalizing the pixel intensity distributions measured on the image sensor CCD2 with respect to the mean intensity of the speckle fields in the same layer. The scale bar in FIG. 4A indicates 200 µm. The width of the normalized histogram becomes narrower for the deeper layers, which indicates speckle reduction as the intensities in the region are smoother. In the meantime, the normalized standard deviations are also calculated for the speckle field in each layer in order to show the intensity variations. As shown in FIG. 4B, the standard deviation reduces by 50% in layer 7, which indicates a significant reduction in speckle in the deepest layer.

FIGS. 4C and 4D illustrate the results of a statistical analysis applied to the speckle fields located in the first layer with different offsets. The scale bar in FIG. 4C indicates 200 µm. As shown in FIG. 4D, the standard deviations show a reduction of 50% in speckle for an offset of approximately 200 µm. This optimal offset for speckle reduction may be dependent upon the scattering properties of the turbid media 42 itself.

FIGS. 5A-5F demonstrate how a spatial offset s may reveal a fine feature obscured by speckle as a consequence of strong scattering. This was demonstrated using the OCT system 2 by taking OCT images from a scattering phantom including polystyrene beads (100 µm in diameter) embedded into a thick layer of butter. Most of the polystyrene beads were located at a depth of 200 µm below the surface.

Figure 5B:
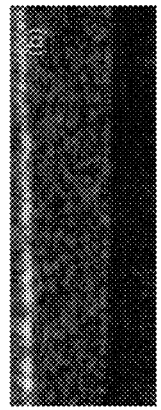
FIG. 5B is a B scan image at the position indicated by the purple dashed line in FIG. 5A.
Figure 5C:
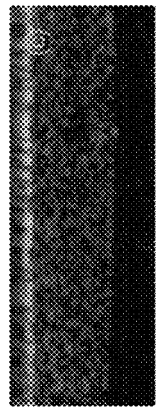
FIG. 5C is a B scan image at the position indicated by the red dashed line in FIG. 5A.
Figure 5E:
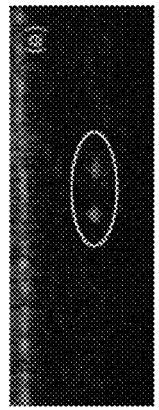
FIG. 5E is a B scan image at the position indicated by the purple dashed line in FIG. 5D.
Figure 5F:
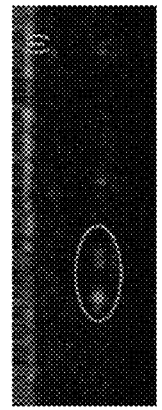
FIG. 5F is a B scan image at the position indicated by the red dashed line in FIG. 5D.
Figure 5A:
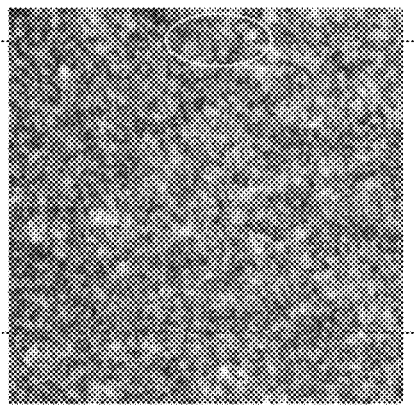
FIG. 5A shows an en face OCT image of 100 μm polystyrene beads at the depth of 200 μm in butter averaged over 1.2 mm to 1.3 mm in optical depth for an offset collection path offset of 0 μm.

As shown in FIGS. 5A-5C, the speckle dominates the conventional OCT images obtained for a spatial offset s=0. Signals from the polystyrene beads are completely obscured by the speckle and as a result most of the beads are not visible in the en face image of FIG. 5A or the B scan images shown in FIGS. 5B and 5C.

Figure 5D:
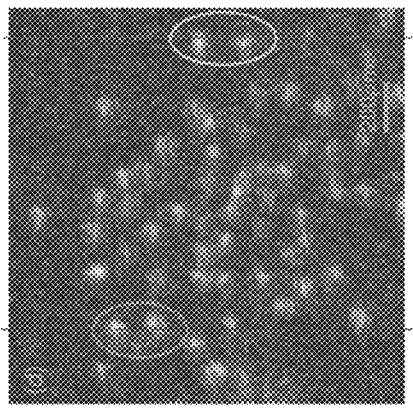
FIG. 5D shows an en face OCT image of 100 μm polystyrene beads at the depth of 200 μm in butter averaged over 1.2 mm to 1.3 mm in optical depth for an offset collection path offset of 80 μm.

As shown in FIGS. 5D-5F, a spatial offset s of 80 µm provides a strong reduction in speckle originating from the butter and therefore clearly reveals the positions of the embedded polystyrene beads. In the B scans shown in FIG. 5E and 5F, the white dots clearly show the presence of beads in the butter due to the improvement in the signal to noise ratio obtained for the spatial offset s of 80 µm.

Experimental Results on Krill and Zebrafish

OCT has great advantages to acquire morphological information from biological samples. However, due to strong scattering in many biological samples, it is difficult to resolve the structures obscured in the speckle. However, by efficiently reducing the contribution from the speckle by applying a spatial offset s between the illumination path 30 and the offset collection path 32, the OCT system 2 is able to reveal those unseen structures.

Figure 6A:
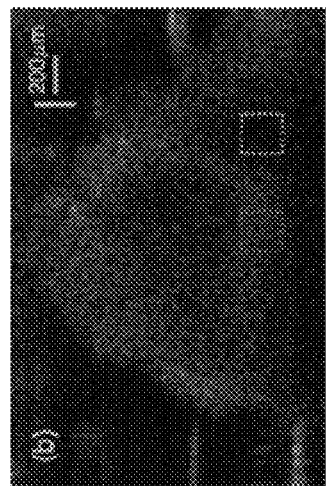
FIG. 6A shows the B scan from an eye ball of an adult krill for an offset collection path offset of 0 μm.
Figure 6B:
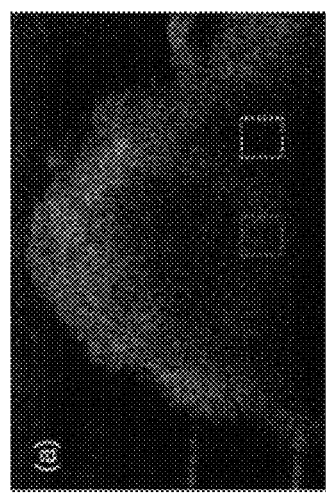
FIG. 6B shows the B scan of the same region of the same eye ball of the same adult krill as the B scan of FIG. 6A for an offset collection path offset of 150 μm.

FIGS. 6A and 6B show the results of a B scan for the case of zero offset (s=0) and a B scan for the case of a 150 µm offset (s=150 µm) on the eye ball of an adult krill respectively. The scale bars in FIG. 6B indicate 200 µm in vertical and horizontal directions. The top surface of the eye ball is well defined in both B scans. However, the bottom surface of the eye ball is not very well defined in FIG. 6A because it is quite difficult for the light to transmit through the eye ball to reach the bottom surface. The strong scattering reduces the signals from the bottom surface. However, as shown in FIG. 6B, the signals from the bottom surface are enhanced when an offset s=150 µm is used. To quantify this improvement, the contrast to noise ratio (CNR) is calculated for the regions indicated by the dashed red box (signal) and the dashed green box (background noise) in the B scans of both FIGS. 6A and 6B where the CNR is defined as:

$$CNR = \frac{|\mu - \mu_b|}{\sqrt{\delta^2 + \delta_b^2}}$$

and where $\mu$, $\delta$, $\mu_b$, $\delta_b$ denote the mean and standard deviation of pixel intensities in the signal region and the background region respectively. A CNR value of 5.93 dB was obtained for the B scan of FIG. 6B with the 150 µm spatial offset. In contrast, a CNR value of 3.35 dB was obtained for the conventional B scan of FIG. 6A with no spatial offset. This demonstrates an enhancement by a factor of 1.77 in the obtained image quality as a result of the 150 µm spatial offset, thereby more clearly revealing the bottom surface of eye ball.

FIGS. 7A and 7B demonstrate the measurement performance of the OCT system 2 for a different biological sample. Specifically, FIGS. 7A and 7B show a B scan performed with no spatial offset (s=0) and a B scan performed with an 80 µm spatial offset (s=80 µm) along the same region of an adult zebra fish which was fixed with formalin solution. The scale bars in FIG. 7B indicate 200 µm in vertical and horizontal directions. The red and green dotted rectangles in FIGS. 7A and 7B indicate the regions of interest used for calculating the Contrast-to-Noise ratio (CNR). The calculated CNR is 0.45 dB for FIG. 7A and 1.29 dB for FIG. 7B.

Due to the strong scattering property of flesh, speckle dominates the area between the surface and the bones as shown in FIG. 7A. Therefore, it is very difficult to find the regions for the spine bones in the noisy OCT image of FIG. 7A (CNR of 0.45 dB). In the B scan shown in FIG. 7B, the speckle is suppressed due to the spatial offset used. As a result, the spine bone structures are revealed more clearly and the contrast is enhanced by a factor of more than two (CNR of 1.29 dB).

Although it is known to reduce the speckle by smoothing image data measured for the case of no spatial offset, it can be difficult to reveal the lost information which was obscured in the speckle. However, as a consequence of the spatial offset s applied between the illumination path and the offset collection path, it is believed that quasi-ballistic photons are preferentially selected or used to create the OCT image and that multiple scattered photons are preferentially rejected so that signals from the region of interest are conserved during collection. Therefore, the CNR may be enhanced without any requirement to perform further processing on the OCT image.

Modifications of the OCT System of FIG. 1A

One of ordinary skill in the art will understand that various modifications are possible to the OCT system 2 of FIG. 1A without departing from the scope of the present invention as defined by the appended claims. For example, the movable coupling lens L2 may be mounted in a lens mount which is attached to a motorized translation stage (not shown). The controller may be configured to control the motorized translation stage so as to vary the spatial offset between the illumination path and the offset collection path to optimize a SNR associated with the OCT image of the sample as a function of depth through the sample.

Alternative OCT Systems

Figure 8A:
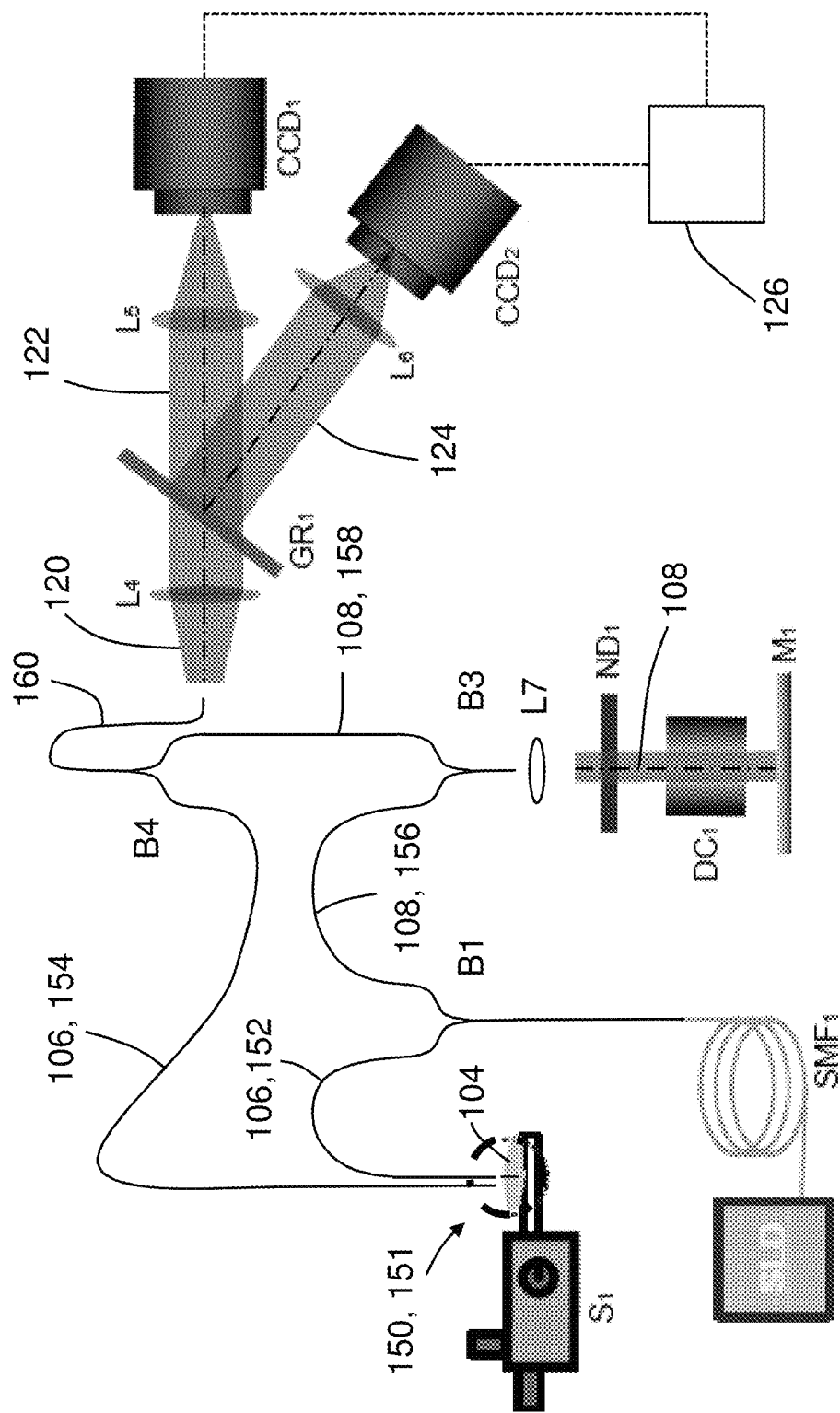
FIG. 8A is a schematic illustration of an alternative OCT system for imaging a sample.

Referring to FIG. 8A there is shown an alternative OCT system generally designated 102 for imaging a sample generally designated 104. The alternative OCT system 102 shares many like features with the OCT system 2 of FIG. 1A and, as such, the features of the alternative OCT system 102 of FIG. 8A are identified using reference numerals which are the same as the reference numerals of the corresponding features of the OCT system 2 of FIG. 1A incremented by "100". The system 102 is configured to couple light from an optical source in the form of a superluminescent diode laser SLD (S850, Superlum, central wavelength 800 nm with bandwidth 14 nm) to the sample 104 and to couple light collected from the sample 104 to first and second detectors in the form of first and second image sensors, CCD1 (CCD camera, FL3-U3-32S2M-CS, Point Grey) and CCD2 (GigE Vision line scan camera, Aviiva EM1,Teledyne).

The system 102 includes a 90/10 transmitting/reflecting optical fibre splitter B1 and a 50/50 transmitting/reflecting optical fibre combiner B4 which together define a Mach-Zehnder interferometer having a measurement arm generally designated 106 including the sample 104, and a separate reference arm generally designated 108. The system 102 further includes a single mode fibre SMF1 and a coupling lens L1 for coupling light from the optical source SLD to the optical fibre splitter B1.

As shown in more detail in FIG. 8B, in the measurement arm 106 between the optical fibre splitter B1 and the sample 104, the system 102 includes a first optical coupling arrangement generally designated 150 which optically couples the optical fibre splitter B1 to the sample 104, and a second optical coupling arrangement generally designated 151 which optically couples the sample 104 to the optical fibre combiner B4.

The first optical coupling arrangement 150 includes an input optical fibre 152 having a microlens 152*a* formed on, or attached to, one end so as to focus incident light 112 onto a surface 144 of the sample 104 along an illumination path 130.

Similarly, the second optical coupling arrangement 151 includes an the output optical fibre 154 having a microlens 154*a* formed on, or attached to, one end for collecting returning light 116 emerging from the surface 144 of the sample 104 along an offset correction path 132.

The optical fibres 152, 154 may be movable laterally relative to one another so as to vary the separation s to the extent permitted by the outer diameters of the optical fibres 152, 154. For example, the alternative OCT system 102 may include one or more translation stages (not shown) for translating one or both of the optical fibres 152, 154 relative to one another so as to vary the separation s.

The system 102 further includes a 3D sample translation stage S1 for translating the sample 104.

In the reference arm 108 between the optical fibre splitter B1 and the optical fibre combiner B4, the system 102 includes a further 50/50 transmitting/reflecting optical fibre splitter B3, a coupling lens L7, a neutral density filter ND1, dispersion compensation DC1, and a fixed reference mirror M1. Although the neutral density filter ND1, the dispersion compensation DC1, and the fixed reference mirror M1 are shown as bulk optical components in FIG. 8A, one of ordinary skill in the art will understand that the neutral density filter ND1, the dispersion compensation DC1, and the fixed reference mirror M1 may be implemented using fibre-optic components thereby avoiding any requirement for the coupling lens L7.

The optical fibre splitter B1 is optically coupled to the optical fibre splitter B3 by an optical fibre 156. Similarly, the optical fibre splitter B3 is optically coupled to the optical fibre combiner B4 by an optical fibre 158.

The system 102 further includes a dispersive element in the form of a transmissive diffraction grating GR1 (1200 lines/mm, coated for 700 to 960 nm), a coupling lens L4 for coupling light from the optical fibre combiner B4 to the diffraction grating GR1, a coupling lens L5 for coupling zero-order diffracted light from the diffraction grating GR1 to the first image sensor CCD1 and a coupling lens L6 for coupling first-order diffracted light from the diffraction grating GR1 to the second image sensor CCD2.

The system 102 further includes a controller 126 configured for communication with the first and second image sensors CCD1 and CCD2.

In use, the optical fibre splitter B1 splits light from the optical source SLD into incident light 112 propagating in the measurement arm 106 and reference light 114 propagating in the reference arm 108. The incident light 112 is focussed into the sample 104 along the illumination path 130 via the input optical fibre 152 and microlens 152a. After interaction with the sample 104, returning light 116 emerges from the sample 104. A portion of the returning light 116, referred to herein as the offset returning light, emerges from the sample 104 along the offset collection path 132 and is collected by the microlens 154a and the output optical fibre 154 and coupled to the optical fibre combiner B4.

The reference light 114 is coupled to the reference mirror M1 via the optical fibre splitter B1, the optical fibre 156, the optical fibre splitter B3, the neutral density filter ND1 and the dispersion compensation DC1. The reference mirror M1 reflects the reference light 114 back through the dispersion compensation DC1, the neutral density filter ND1, the optical fibre splitter B3 and is coupled to the optical fibre combiner B4 by the optical fibre 158. In all other respects, the operation of the alternative OCT system 102 of FIG. 8A is identical to the operation of the OCT system 2 of FIG. 1A described above.

In a variant of the alternative OCT system 102 of FIG. 8A, the microlenses 152a, 154a may be replaced with GRIN lenses.

One of ordinary skill in the art will understand that it is possible to modify the OCT system described above with reference to FIGS. 8A and 8B without departing from the scope of the present invention as defined by the appended claims. For example, FIG. 8C shows an alternative optical coupling arrangement generally designated 250 for use with a modified OCT system. The optical coupling arrangement 250 includes a central optical fibre 252 and a plurality of surrounding optical fibres 254 arranged circumferentially around the central optical fibre 252. The optical coupling arrangement 250 further includes a GRIN lens 252a located at the end of the central optical fibre 252 to focus light from the central optical fibre 252 onto a region of interest 240 and GRIN lenses 254a located at the ends of the surrounding optical fibres 254 for collecting offset returning light emerging from a plurality of regions of the sample located circumferentially around the region of interest 240. One of ordinary skill in the art will understand how to interfere the returning light collected in each of the surrounding optical fibres 254 with the reference light to form an OCT image.

In a variant of the optical coupling arrangement shown in FIG. 8C, the direction of the illumination may be reversed such that light is focussed from the surrounding optical fibres 254 onto a plurality of regions of interest and offset returning light emerging from a central region 240 of the sample is collected by the central optical fibre 252 and is interfered with reference light to form an OCT image of the regions of interest.

In a further variant of the optical coupling arrangement shown in FIG. 8C, the GRIN lenses 252a, 254a may be omitted altogether.

One of ordinary skill in the art will also understand that although the offset collection paths 32, 132 in the OCT systems described above are parallel to, but spatially offset from, the illumination paths 30, 130, the offset collection paths 32, 132 need not be parallel to the illumination paths 30, 130. For example, light from an optical source may be focussed so as to form incident light which propagates along an illumination path and which converges on a region of interest of the sample, and the offset returning light may emerge from the sample along an offset collection path which is spatially offset from the region of interest of the sample but which is not parallel to the illumination path.

FIG. 8D shows a further alternative optical coupling arrangement generally designated 350 for use with a modified OCT system. The optical coupling arrangement 350 includes a multi-mode optical fibre 352 for illuminating a region of interest 340 of a sample and for collecting offset returning light emerging from the sample. One of ordinary skill in the art will understand that it is possible to characterize the multi-mode optical fibre 352 in terms of phase and, optionally, also in terms of amplitude and/or polarization by measuring the amplitude and phase distribution of one or more polarization components of an output optical field on an output side of the multi-mode optical fibre 352 for a plurality of input optical fields on an input side of the multi-mode optical fibre 352, wherein each input optical field is orthogonal to the other input optical fields. Each input optical field may, for example, be orthogonal to the other input optical fields in at least one of phase, amplitude and polarization. For example, one of ordinary skill in the art will understand that the OCT system may comprise a diffractive optical element (not shown), such as a spatial light modulator or a digital micromirror array and, optionally, one or more polarization control elements (not shown) at an input side of the multi-mode optical fibre 352 and one or more polarization control elements (not shown) and an image sensor (not shown) at an output side of the multi-mode optical fibre 352 for characterization of the multi-mode optical fibre 352. Once the multi-mode optical fibre 352 is characterized, the one or more polarization control elements (not shown) and the image sensor (not shown) at the output side of the multi-mode optical fibre 352 may be removed and the sample positioned at the output side of the multi-mode optical fibre 352.

One of ordinary skill in the art will also understand that once the multi-mode optical fibre 352 is characterized in terms of phase and, optionally, also in terms of amplitude and polarization to generate characterization results, the characterization results may be used to generate a desired output optical field on an output side of the multi-mode optical fibre 352 by controlling the phase and, optionally also the amplitude and polarization of the input optical field. For example, one of ordinary skill in the art will understand that, once the multi-mode optical fibre 352 has been characterized in terms of phase and, optionally, also in terms of amplitude and polarization as described above, the multi-mode optical fibre 352 may be used to transmit light from an input side of the multi-mode optical fibre 352 through the multi-mode optical fibre 352 and focus the transmitted light onto the region of interest 340 of a sample whilst also collecting offset returning light emerging from an annular region of the sample located around the region of interest 340 as shown in FIG. 8D and transmitting the returning light back through the multi-mode optical fibre 352 to an input side of the multi-mode optical fibre 352. One of ordinary skill in the art will also understand how to combine the returning light collected by the multi-mode optical fibre 352 with the reference light to form an OCT image.

In a variant of the optical coupling arrangement shown in FIG. 8D, the direction of the illumination may be reversed such that light exits the multi-mode optical fibre 352 so as to illuminate an annular region of interest of the sample and offset returning light emerging from a central region 340 of the sample is collected by the multi-mode optical fibre 352 and is interfered with reference light to form an OCT image of the annular region of interest.

One of ordinary skill in the art will understand that it is possible to further modify the OCT systems described above with reference to FIGS. 1A and 8A without departing from the scope of the present invention as defined by the appended claims. For example, the optical source may comprise a broadband light source other than a superluminescent diode laser. For example, the optical source may comprise an LED such as a superluminescent LED.

Alternatively, the optical source may comprise a narrow-band light source or a coherent light source such as a laser or an OPO.

The first and second detectors may comprise first and second single pixel detectors such as first and second photodiodes or the like.

The optical source may be tunable and the controller may be configured to:

vary a wavelength of the optical source;

use one of the first and second detectors to detect the interference as a function of wavelength of the optical source to provide an optical spectrum of the interference; and use an inverse Fourier transform to convert the optical spectrum of the interference into an OCT image of the sample as a function of depth through the sample.

The OCT system may comprise a variable optical element configured to vary an optical length of the reference path. For example, the mirror M1 may be movable. The wavelength of the optical source may be fixed and the controller may be configured to:

control the variable optical element so as to vary an optical length of the reference path across a range of optical lengths selected to match a range of depths in the sample; and use one of the first and second detectors to detect the interference as a function of the optical length of the reference path to provide an OCT image of the sample as a function of depth through the sample.

The invention claimed is:

1. An optical coherence tomography system for use in imaging a sample, the system comprising:
   an optical splitter having an input configured to be optically coupled to an optical source, a measurement output, and a reference output;
   an optical coupling lens configured to illuminate a region of interest of the sample with incident light and to collect offset returning light emerging from the sample along an offset collection path, wherein the incident light is received from the optical source via the measurement output of the optical splitter, wherein the incident light is incident on the sample along an illumination path, and wherein the offset collection path is spatially offset from the region of interest of the sample and is parallel to, but spatially offset from, the illumination path;
   an offset lens; and
   an optical combiner having a measurement input, a reference input, and an output configured to be optically coupled to an optical detector,
   wherein the measurement output of the optical splitter and the measurement input of the optical combiner define a measurement arm therebetween, and the reference output of the optical splitter and the reference input of the optical combiner define a reference arm therebetween, the reference arm being separate from the measurement arm,
   wherein the sample and the optical coupling lens are located in the measurement arm,
   wherein the reference arm defines a reference path for reference light,
   wherein the offset lens is located in the measurement arm between the optical coupling lens and the optical combiner so as to optically couple the offset returning light to the optical combiner so that the optical combiner combines the reference light with the offset returning light to form combined light for detection at the optical detector so that the optical detector detects interference between the offset returning light and the reference light, and
   wherein the offset lens defines an offset lens optical axis, the combined light propagates along a combined light optical axis, and the offset lens optical axis is parallel to, but spatially offset from, the combined light optical axis.

2. The system according to claim 1, wherein the incident light converges as it is incident on the sample.

3. The system according to claim 1, wherein the offset returning light diverges as it emerges from the sample along the offset collection path so as to define a virtual image point in the sample on the offset collection path, the virtual image point being spatially offset from the region of interest.

4. The system according to claim 1, comprising the optical source and/or the optical detector.

5. The system according to claim 1, wherein the optical splitter and the optical combiner define a Mach-Zehnder interferometer.

6. The system according to claim 1, wherein the optical coupling lens comprises an objective lens.

7. The system according to claim 1, comprising a lens mount and a translation stage, wherein the lens mount is attached to the translation stage, the offset lens is mounted in the lens mount, and the translation stage is operable so as to move the offset lens so as to vary the spatial offset between the offset lens optical axis and the combined light optical axis and thereby vary the spatial offset between the offset collection path and the region of interest.

8. The system according to claim 7, the translation stage is operable so as to move the offset lens so as to reduce the spatial offset between the offset lens optical axis and the combined light optical axis to zero and thereby reduce the spatial offset between the offset collection path and the region of interest to zero.

9. The system according to claim 1, wherein the optical source comprises a broadband light source and wherein the optical detector comprises an image sensor.

10. The system according to claim 9, comprising:
a dispersive element; and
a controller configured for communication with the image sensor,
wherein the dispersive element is configured to spatially disperse the interference across the image sensor according to a wavelength of the interference, the image sensor is configured to detect the spatial distribution of the spatially dispersed interference and the controller is configured to use an inverse Fourier transform to convert the spatial distribution of the detected spatially dispersed interference into an optical coherence tomography image of the sample as a function of depth through the sample.

11. The system according to claim 10, comprising first and second image sensors, wherein the dispersive element comprises a diffraction grating and wherein the diffraction grating and the first and second image sensors are arranged relative to one another for optical coupling of zero-order diffracted light to the first image sensor and higher-order diffracted light to the second image sensor.

12. The system according to claim 1, wherein the optical source comprises a narrowband light source or a coherent light source.

13. The system according to claim 12, wherein the optical source is tunable and the system further comprises a controller configured for communication with the optical detector and the optical source, wherein the controller is configured to:
vary a wavelength of the optical source;
use the optical detector to detect the interference as a function of wavelength of the optical source to provide an optical spectrum of the interference; and
use an inverse Fourier transform to convert the optical spectrum of the interference into an optical coherence tomography image of the sample as a function of depth through the sample.

14. The system according to claim 12, comprising:
a variable optical element configured to vary an optical length of a reference path for the reference light; and
a controller configured for communication with the optical detector and the variable optical element, wherein the controller is configured to:
control the variable optical element so as to vary the optical length of the reference path across a range of optical lengths selected to match a range of depths in the sample; and
use the optical detector to detect the interference as a function of the optical length of the reference path to provide an optical coherence tomography image of the sample as a function of depth through the sample.

15. The system according to claim 9, wherein the broadband light source comprises a superluminescent laser diode or a light emitting diode.

16. The system according to claim 11, wherein the higher-order diffracted light comprises first-order diffracted light.

17. The system according to claim 12, wherein the narrowband light source or the coherent light source comprises a laser or an optical parametric oscillator.

18. The system according to claim 14, wherein the variable optical element comprises a movable mirror.

19. An optical coherence tomography method for use in imaging a sample, the method comprising:
using an optical splitter to split light received from an optical source into measurement light and reference light;
using an optical coupling lens to illuminate a region of interest of the sample with the measurement light and to collect offset returning light emerging from the sample along an offset collection path which is spatially offset from the region of interest of the sample, wherein the measurement light is incident on the sample along an illumination path and the offset collection path is parallel to, but spatially offset from, the illumination path; and
using an offset lens located between the optical coupling lens and an optical combiner so as to optically couple the offset returning light to the optical combiner so that the optical combiner combines the reference light with the offset returning light to form combined light for detection at an optical detector so that the optical detector detects interference between the offset returning light and the reference light,
wherein the offset lens defines an offset lens optical axis, the combined light propagates along a combined light optical axis, and the offset lens optical axis is parallel to, but spatially offset from, the combined light optical axis.

20. An optical coherence tomography system for use in imaging a sample, the system comprising:
an optical splitter having an input configured to be optically coupled to an optical source, a measurement output, and a reference output;
an optical coupling lens configured to illuminate a region of interest of the sample with incident light received from the optical source via the measurement output of the optical splitter and to collect offset returning light emerging from the sample along an offset collection path which is spatially offset from the region of interest of the sample;
an offset lens; and
an optical combiner having a measurement input, a reference input, and an output configured to be optically coupled to an optical detector,
wherein the measurement output of the optical splitter and the measurement input of the optical combiner define a measurement arm therebetween, and the reference output of the optical splitter and the reference input of the optical combiner define a reference arm therebetween, the reference arm being separate from the measurement arm,
wherein the sample and the optical coupling lens are located in the measurement arm,
wherein the reference arm defines a reference path for reference light,
wherein the offset lens is located in the measurement arm between the optical coupling lens and the optical combiner so as to optically couple the offset returning light to the optical combiner so that the optical combiner combines the reference light with the offset returning light to form combined light for detection at the optical detector so that the optical detector detects interference between the offset returning light and the reference light, and wherein the offset lens defines an offset lens optical axis, the combined light propagates along a combined light optical axis, and the offset lens optical axis is parallel to, but spatially offset from, the combined light optical axis.

21. An optical coherence tomography method for use in imaging a sample, the method comprising:

using an optical splitter to split light received from an optical source into measurement light and reference light;

using an optical coupling lens to illuminate a region of interest of the sample with the measurement light and to collect offset returning light emerging from the sample along an offset collection path which is spatially offset from the region of interest of the sample; and using an offset lens located between the optical coupling lens and an optical combiner so as to optically couple the offset returning light to the optical combiner so that the optical combiner combines the reference light with the offset returning light to form combined light for detection at an optical detector so that the optical detector detects interference between the offset returning light and the reference light, wherein the offset lens defines an offset lens optical axis, the combined light propagates along a combined light optical axis, and the offset lens optical axis is parallel to, but spatially offset from, the combined light optical axis.

* * * * *